United States Patent [19]

Becker et al.

[11] 4,090,847

[45] May 23, 1978

[54] DETERMINING FIRE RETARDANCY

[75] Inventors: Ralph S. Becker, Houston, Tex.; Roger W. Fenstermaker; Jack P. Guillory, both of Bartlesville, Okla.

[73] Assignee: Phillips Petroleum Company, Bartlesville, Okla.

[21] Appl. No.: 751,500

[22] Filed: Dec. 17, 1976

[51] Int. Cl.² .................. G01N 21/26; G01N 23/12
[52] U.S. Cl. ........................ 23/230 R; 23/254 R; 250/432 R
[58] Field of Search ............ 23/230 R, 232 C, 232 R, 23/232 E, 254 R, 254 E, 255 R, 255 E; 73/23.1; 250/373, 432

[56] References Cited

U.S. PATENT DOCUMENTS

| 2,736,813 | 2/1956 | Cherrier | 250/373 |
| 2,878,388 | 3/1959 | Bergson | 250/373 |
| 3,710,111 | 1/1973 | Collura | 250/373 |

Primary Examiner—Robert M. Reese

[57] ABSTRACT

A composition is tested for its flame retarding ability by determining the decrease in the amount of hydrogen molecules produced in a reaction zone from hydrogen radicals when said composition is present in the reaction zone over the amount produced in the same reaction zone without said composition.

13 Claims, 1 Drawing Figure

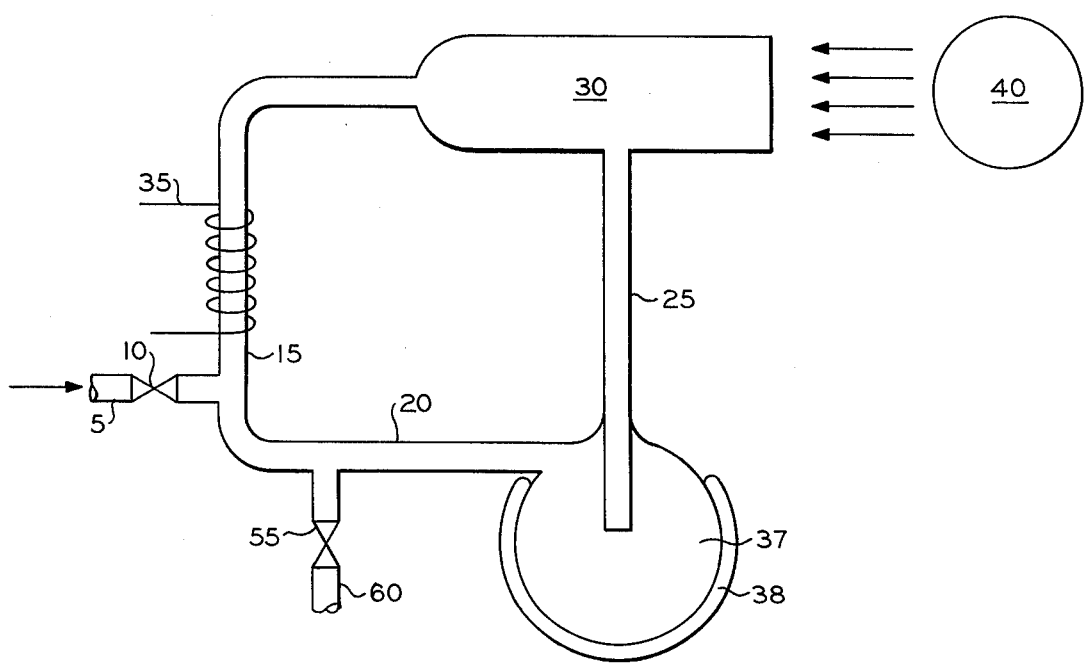

DETERMINING FIRE RETARDANCY

BACKGROUND OF THE INVENTION

This invention relates to testing of compositions for flame retardancy. In particular, it pertains to testing a composition for its flame retarding ability by measuring its propensity to scavenge hydrogen radicals.

The continuing introduction of new synthetic resins, rubbers, fibers, plastics, and composites necessitates testing "fire resistance" of an increasing number of these materials prior to their replacement of traditionally used materials. Government regulations require certain products to be made of "fire resistant" materials (a partial list of fire safety regulations is listed in U.S. Pat. No. 3,974,310), but even if the product is not required by law to be "fire resistant," such quality is sought by an increasing number of consumers and industrial purchasers. Certain compositions, termed throughout this disclosure as fire retardants, when incorporated into materials tend to improve their fire resistance. It is very difficult to predict whether a composition possesses a fire retarding property. For example, antimony is not by itself effective as a fire retardant; however, when it is combined with a halogen, it is an excellent fire retardant. Consequently, millions of dollars are spent by industry each year for evaluating potential fire retardant compositions. To evaluate a fire retardant composition by a traditional method such as Underwriters Laboratories, Inc. tests 94VE-D, 94VE-1, and 94VE-2 (described in Tests for Flammability of Plastic Materials, Underwriters Lab., Inc., 2nd Ed., pages 6, 7, and 8), the composition is incorporated into a material which is then burned in controlled conditions. A variety of other tests (compiled, for example, in John W. Lyons, *The Chemistry and Uses of Fire Retardants*, J. W. Wiley, Interscience, N.Y. 1970) is based upon first incorporating a potential fire retardant into a material and testing the fire resistance of the material to determine the effectiveness of the fire retardant.

This invention obviates some of the problems encountered in testing compositions for their fire retardancy by providing an improved method for carrying out these tests.

Thus, one object of the present invention is to provide a method for testing fire retardant ability of compositions without the need of first incorporating said composition into the material the fire resistance of which is sought to be improved.

Another object of the invention is to provide a method for rapid and efficient screening of compositions for their fire retarding ability.

Still another object of the invention is to provide an inexpensive method for rapid and efficient testing fire retardancy of compositions.

A further object of the invention is to provide an efficient and quick to perform method for testing fire retardancy of compositions and fire resistance of materials which does not require flame combustion.

Other objects of the invention will become apparent to those skilled in the art upon studying this disclosure.

SUMMARY OF THE INVENTION

In accordance with one aspect of the invention a composition is placed in a reaction zone containing hydrogen radicals. The decrease in the amount of hydrogen when the composition is in the reaction zone over the situation when the reaction zone is free of such composition is then determined. The decrease is directly proportional to fire retardancy of the composition tested.

In accordance with another aspect of the invention, there is provided a device for carrying out the process of the present invention. The device comprises a chamber having an inlet and an outlet, a source of electromagnetic radiation and means for introducing gases into the reaction chamber and for withdrawing products therefrom.

In accordance with a further aspect of the invention, the device for determining the fire retarding ability of a composition comprises a chamber having at least one wall adapted to transmit electromagnetic radiation from a source located outside and in the proximity of the chamber.

In accordance with a still further aspect of the invention, the device for determining the fire retarding ability of a composition includes a chamber having a source of electromagnetic radiation therein, an inlet to and an outlet from the reaction chamber.

In accordance with still another aspect of the invention, the device for determining the fire retarding ability of a composition includes a reaction chamber having an inlet and an outlet, first means for introducing gases to the reaction chamber, second means for withdrawing the products from the reaction chamber, a source of electromagnetic radiation for irradiating the gases contained in the reaction chamber, a conduit communicating at its end with the reaction chamber and third means for circulating gases through the chamber and the conduit.

In accordance with still another aspect of the invention, a compound which when irradiated decomposes to produce hydrogen radicals is placed in a reaction zone and irradiated therein by electromagnetic radiation having the wavelength selected to produce said decomposition. The amount of hydrogen produced after hydrogen radicals combine is measured. The reaction zone is then evacuated and the procedure is repeated except that a composition which is sought to be tested for its fire retarding properties is introduced together with the source compound into the reaction zone. The irradiation step is then repeated and the amount of hydrogen molecules produced is measured. The fire retarding ability is directly proportional to the difference between the amount of hydrogen produced in the absence of the composition and in the presence of it in the reaction zone.

Other aspects of the invention will become apparent to those skilled in the art upon studying this disclosure and the appended claims.

BRIEF DESCRIPTION OF THE DRAWING

The FIGURE depicts a device which is suitable for carrying out the process of this invention.

DETAILED DESCRIPTION OF THE INVENTION

Hydrogen radicals are believed to be one of the initiating species in flame combustion. It has been discovered that a composition can be tested for fire retardancy by permitting it to react with hydrogen radicals having similar amounts of kinetic energy as those in a combustion zone and determining the amount of hydrogen radicals removed by the reaction. The amount of hydrogen radicals removed or scavenged by the composition is directly proportional to the fire retardancy of that composition. Thus, numerous compositions which are potentially fire retardant can be tested quickly and efficiently without the need for incorporating said compositions into a material and then testing the fire resistance of the material.

Hydrogen radicals can be produced in the reaction zone by any method. One method (described in Journal of Molecular Evolution, Volume 4, page 160 1974) produces hydrogen radicals by irradiation of $H_2S$ or $CH_3SH$ with electromagnetic radiation having a frequency in the ultraviolet range. The hydrogen radicals (hot hydrogen atoms) are produced in accordance with the following reactions:

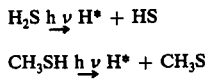

where H* designates a hot hydrogen radical. It is believed that compounds having the general formula RSH where R is hydrogen or alkyl are suitable for production of hydrogen radicals when irradiated with ultraviolet radiation. Other compounds which can produce hydrogen radicals by photolysis include hydrogen halides such as HI and HBr, $NH_3$, and $CH_4$.

The reaction zone is maintained at a sufficiently high temperature and a sufficiently low pressure to retain the tested composition in the gaseous state but the temperature and pressure should be such as to prevent decomposition of the tested composition. Normally the reaction is carried out at temperatures from about 30° C (86° F) to about 50° C (122° F). The pressure in the reaction zone varies from about 5 torr to about 760 torr.

The wavelength of the electromagnetic radiation must be such as to break up the molecules of the source compound to produce hydrogen radicals. Generally, the wavelength falls within the ultraviolet range (about 2000 A – 4000 A); wavelengths frequencies between about 2000 A and about 3000 A are particularly useful. It is preferred to utilize wavelengths at which the potential fire retardant does not absorb radiation. Otherwise the amount of radiation absorbed by the potential fire retardant should be determined to correct the results for this effect. Any ultraviolet energy source can be utilized in carrying out the process of this invention. Usually a mercury arc lamp, tunable dye laser, or any other laser capable of producing ultraviolet light is used. The amount of H* source compound should be sufficient to produce enough hydrogen radicals when irradiated by ultraviolet radiation to obtain a measurable quantity of hydrogen molecules or hydrogen radicals when the fire retardant composition is in the reaction zone. Since hydrogen radicals produced by irradiation and not scavenged by the fire retardant composition combine to produce hydrogen molecules, the amount of hydrogen radicals scavenged by the fire retardant composition can be determined by measuring the amount of hydrogen molecules produced in the reaction zone. The amount of hydrogen molecules can be measured by any suitable method including a chromatographic analysis. Alternatively, liquid $N_2$ can be used to remove all compounds except for hydrogen from the gaseous phase and the amount of hydrogen produced in the reaction can be determined simply by measuring the pressure in the reaction zone.

In operation, H* source compound is introduced into the reaction zone and irradiated at preselected conditions with radiation of predetermined wavelength. The hydrogen radicals produced by irradiation are allowed to combine to form hydrogen molecules. The gas in the reaction zone is then tested to determine the amount of hydrogen molecules produced.

The reaction zone is then evacuated and the procedure repeated at exactly the same conditions except that a fire retardant composition sought to be tested is introduced into the reaction zone together with the H* source compound. The H* source compound is again irradiated in exactly the same manner and the amount of hydrogen molecules in the reaction zone is measured.

Alternatively, if all H* source compound is used up for production of hydrogen radicals, the amount of hydrogen molecules produced in the reaction zone in the absence of fire retardant composition can be calculated and only the reaction with the fire retardant composition in the reaction zone needs to be performed. It is preferred to conduct a two-step test because it may be difficult to estimate whether the irradiation resulted in complete conversion of the H* source compound and because a small portion of hydrogen radicals may combine with other materials. Side reactions will not appreciably affect the results in the two-step process because any side reaction effect will be present in both steps of the process and therefore will not affect the difference.

If the fire retardant absorbs radiations at the wavelength used for the production of hot hydrogen radicals, the retardant is first tested to measure its absorption capacity. Any suitable means for measuring electromagnetic absorption can be used; usually ultraviolet spectrophotometers such as those made by Perkin-Elmer, Cary, or Hewlett-Packard are used for this purpose.

For example, if the measurement is made for absorption of radiation at 3371 A which is used to produce H* from $H_2S$ and it is determined that a particular fire retardant absorbs 50 percent of the light, it is necessary to multiply the amount of hydrogen produced in the run which included fire retardant by 1/0.5 to account for the fact that 50 percent of the radiation was absorbed and, therefore, not able to produce hot hydrogen radicals. Of course, if the potential fire retardant composition does not absorb radiation at the frequency at which the hot hydrogen radicals are produced, no correction is required.

Referring now to the FIGURE, H* source compound, such as $H_2S$, is introduced into evacuated fire retardancy testing device via conduit 5. H* source compound is allowed to pass through an open valve 10 and permitted to flow either via leg 15 or via horizontal tube 20 and a vertical tube 25 into the reaction zone 30. The valve 10 is then closed. The circulation of gas through reaction volume which includes the reaction zone 30, the leg 15, a horizontal tube 20, and the vertical tube 25 is provided by creating at temperature gradient between leg 15 heated by coils 35 wrapped around a portion of the leg 15 and cold trap 37 cooled by ice water bath 38. The $H_2S$ gas is decomposed by electromagnetic radiation in the ultraviolet range emitted from the source 40 and penetrating the reaction zone 30 as shown. The radiation causes decomposition of $H_2S$ into hot hydrogen radicals and sulfur. The trap 37 is maintained at a temperature of about 0° C (32° F) by submerging it in an ice water bath 38. Hydrogen radicals produced by the irradiation combine to produce hydrogen molecules. Upon the completion of the conversion of $H_2S$, a valve 55 is opened and the products are withdrawn from the reaction volume via passageway 60 and analyzed to determine the amount of hydrogen present.

The sulfur is removed from the irradiation system and the reaction volume is evacuated. A gaseous composition which is sought to be tested for its fire retardancy is introduced into the reaction volume via 5 by opening valve 10. $H_2S$ is then added until the pressure inside the reaction volume reaches the pressure under which $H_2S$ was irradiated in the first step. Gases are then irradiated under exactly the same conditions as in step (1), producing hydogen radicals. Some of the hydrogen radicals are scavenged by the composition preventing these from combining into hydrogen molecules. Others combine to form hydrogen molecules. Upon completion of the conversion of $H_2S$, valve 55 is opened and gaseous products are withdrawn by 60. Gaseous products withdrawn from the reaction volume are then analyzed to determine the amount of hydrogen present therein.

The amount of hydrogen molecules produced in the reaction volume when the fire retardant composition was present therein is then adjusted to account for a slightly lower amount of $H_2S$ available (to keep the pressure inside the reaction volume the same as in the first step) and subtracted from the amount of hydrogen molecules present in the first step. The difference is directly proportional to the fire retardancy of the composition tested.

This procedure can be used to compare the fire retardancy of the tested composition to a composition having known fire retardancy or it can be correlated with standard tests for fire resistance so as to allow estimation of fire resistance from a measurement of fire retardancy.

Many modifications will become apparent to those skilled in the art upon studying this disclosure. Such modifications that fall within the spirit of this invention are intended to be included within its scope. The examples are included merely for illustrative purposes and are not intended to limit the scope of the invention in any manner.

EXAMPLE I

The volume of a quartz reactor shown in the FIGURE was 305 ml. The length of the reaction zone was 9.7 cm. The air was evacuated from the reactor volume, then $H_2S$ was introduced therein until the pressure inside reached 498 mm Hg. To promote circulation of gas through the reactor volume the arm of the reactor was maintained at temperatures between 138° C and 154° C (280°–310° F) and a cold bath 38 maintained at about 0° (32° F). Radiation from a power lamp operating on a direct current of 3.45 amperes and 53 volts, warmed up for 45 minutes, was then permitted to penetrate for 2 hours the reaction zone from the direction indicated in the FIGURE. A cloud of sulfur formed immediately upon beginning of irradiation; the sulfur was allowed to continuously settle into the trap containing $H_2O$.

The analysis of the gas in the reaction volume revealed the presence of 1.66 mole percent $H_2$.

The reaction volume was then evacuated and filled with $H_2S$ until the pressure reached 250 mm Hg. $CF_3Br$, a known fire retardant, was then introduced into the reaction volume until the pressure reached 275 mm Hg. More $H_2S$ was then charged into the reaction volume until the pressure therein reached 500 mm. To promote circulation of gases through the reaction volume the arm of the reactor was heated so that its temperature was maintained between 138° C and 154° C (280°–310° F). The radiation from a power lamp operating on a direct current of 3.5 amperes and 52 volts, warmed up for 30 minutes, was permitted to penetrate for 2 hours the reaction zone from the direction indicated on the FIGURE. Upon completion of irradiation, the pressure inside the reaction volume was 499 mm Hg. A cloud of sulfur formed immediately upon beginning of irradiation; the sulfur was allowed to continuously settle into the trap containing $H_2O$. Analysis of the gas in the reaction volume revealed the presence of 1.35 mole percent $H_2$.

Since if $CF_3Br$ acted only to dilute the $H_2S$ the concentrate of $H_2$ in the gas would have been 1.58 mole percent, it can be concluded that $CF_3Br$ removed or scavenged some of H* (hydrogen radicals) thus preventing the formation of $H_2$.

We claim:

1. A method for testing flame retarding ability of a composition which comprises:
    (a) producing in a reaction zone hot hydrogen radicals;
    (b) allowing hot hydrogen radicals to combine forming hydrogen molecules;
    (c) measuring the amount of hydrogen molecules formed in step (b);
    (d) repeating steps (a)–(b) under the same conditions but in the presence of the composition in gaseous state in the reaction zone; and
    (e) determining the differrence between the amount of hydrogen molecules measured in step (c) and a corresponding part of step (d).

2. A method as claimed in claim 1 wherein the step of producing comprises subjecting a compound selected from the group consisting of $H_2S$ and $CH_3SH$ to radiation having the wavelength in the range from about 2000 A to about 4000 A and intensity sufficient to produce a measurable amount of hydrogen radicals.

3. A method as claimed in claim 1 wherein the step of producing comprises subjecting $NH_3$ or $CH_4$ to radiation having wavelength in the range from about 2000 A to about 4000 A and intensity sufficient to produce a measurable amount of hydrogen radicals.

4. A method as claimed in claim 1 wherein the step of producing comprises:
    subjecting a compound having formula RSH where R is hydrogen or alkyl to radiation of such intensity and wavelength and for such a period of time as to produce sufficient amount of hot hydrogen radicals to permit measurements in steps (c) and (d).

5. A method as claimed in claim 4 wherein the temperature and pressure in the reaction zone are such as to retain the composition in a gaseous state without causing thermal decomposition thereof.

6. A method as claimed in claim 4 wherein the measuring step includes analyzing by gas chromatography.

7. A method as claimed in claim 4 wherein the measuring step comprises:
    separating $H_2$ from other compounds by cooling the reaction zone with liquid nitrogen to liquefy or solidify said compounds and
    determining the pressure exerted by $H_2$.

8. A method as claimed in claim 4 wherein the radiation has a wavelength at which the composition essentially absorbs no radiation.

9. A method as claimed in claim 4 further comprising measuring the amount of radiation absorbed by the composition and adjusting the differences of step (e) to take into account absorption by the composition.

10. A method as claimed in claim 4 further comprising:

measuring the absorbency value of the radiation having the same wavelength as that used to produce hot hydrogen radicals; and dividing the absorbency value into the amount of hydrogen obtained in step (d).

11. A method as claimed in claim 10 wherein the absorbency of the composition is measured by an ultraviolet spectrophotometer.

12. A self-contained cyclic system for determining the fire retarding ability of a composition comprising, in combination:

an enclosed reaction chamber having an inlet and an outlet and at least one wall capable of transmitting electromagnetic waves having wavelengths from about 2000 A to about 4000 A from the exterior to the interior of said chamber;

a source of electromagnetic radiation capable of producing wavelengths from about 2000 A to about 4000 A which is in close proximity to said one wall of said chamber and so positioned as to pass electromagnetic waves through said one wall into the interior of said chamber;

a conduit connected to said inlet and said outlet of said chamber and communicating at its ends with the interior of said reaction chamber to provide a cyclic flowpath for gases between said reaction chamber and through said conduit;

a heater placed around one portion of said conduit;

a cooling jacket placed around another portion of said conduit, said heater and cooling jacket promoting the circulation of gases enclosed in the reaction chamber and in said conduit;

an inlet conduit means in open communication with said conduit and having a valve for selectively opening and closing said inlet conduit means providing an inlet for the introduction of said composition into said system; and an outlet conduit means in open communication with said conduit having a valve for selectively opening and closing said conduit means to provide an outlet for withdrawal of said composition after determining the fire retarding ability of said composition.

13. A self-contained cyclic system for determining the fire retarding ability of a composition comprising, in combination:

an enclosed reaction chamber having an outlet and an inlet;

a source of electromagnetic radiation capable of producing wavelengths from about 2000 A to about 4000 A within said chamber;

a conduit connected to said inlet and said outlet and communicating at its ends with said reaction chamber to provide a cyclic flowpath for gases between said reaction chamber and through said conduit;

a heater placed around one portion of said conduit;

a cooling jacket placed around another portion of said conduit, said heater and cooling jacket being used to promote the circulation of gases enclosed in the reaction chamber and said conduit;

an inlet conduit means in open communication with said conduit and having a valve for selectively opening and closing said inlet conduit means to provide an inlet for the introduction of said composition into said system; and an outlet conduit means in open communication with said conduit and having a valve for selectively opening and closing said outlet conduit means to provide an outlet for the withdrawal of said composition from said system after determining the fire retarding ability of said composition.

* * * * *